United States Patent [19]

Dannels

[11] 3,992,274
[45] Nov. 16, 1976

[54] SENSITIZED PRODUCTION OF SULFHYDRYL COMPOUNDS USING ULTRA VIOLET RADIATION

[75] Inventor: Bobby F. Dannels, Grand Island, N.Y.

[73] Assignee: Hooker Chemicals & Plastics Corporation, Niagara Falls, N.Y.

[22] Filed: Dec. 23, 1974

[21] Appl. No.: 535,632

[52] U.S. Cl. ............... 204/158 R; 204/159.18; 204/162 R; 260/42.37; 260/79; 260/830 S
[51] Int. Cl.² ................................ B01J 1/10
[58] Field of Search ........ 204/159.18, 162 R, 158 R

[56] References Cited
UNITED STATES PATENTS

| | | | |
|---|---|---|---|
| 2,398,481 | 4/1946 | Vaughan et al. | 204/163 |
| 2,411,983 | 12/1946 | Vaughan et al. | 204/163 |
| 2,873,239 | 2/1959 | Nummy et al. | 204/158 |
| 3,398,200 | 8/1968 | Griesbaum et al. | 260/609 |
| 3,412,001 | 11/1968 | Edwards | 204/162 |
| 3,488,270 | 1/1970 | Griesbaum et al. | 204/162 |

*Primary Examiner*—Richard B. Turer
*Attorney, Agent, or Firm*—Peter F. Casella; James F. Mudd; David A. Stein

[57] ABSTRACT

An improved process for production of sulfhydryl-terminated compounds by reaction of an allene compound and hydrogen sulfide is disclosed wherein the reaction is carried out in the presence of ultraviolet light of wavelength substantially above 2600 Angstroms and of an organic photosensitizing reagent to obtain a substantially colorless product of improved purity at an increased reaction rate. The invention also includes polymerization of the crude sulfhydryl-terminated product with an unsaturated compound to prepare sulfhydryl-terminated polythioethers which are useful as chemical intermediates and precursors of elastomeric sealants, such as architectural sealants.

13 Claims, No Drawings

SENSITIZED PRODUCTION OF SULFHYDRYL COMPOUNDS USING ULTRA VIOLET RADIATION

BACKGROUND OF THE INVENTION

1. Field of the Invention

The invention relates to improvements in the manufacture of sulfhydrylterminated compounds useful as chemical intermediates and precursors of polythioether elastomeric sealants. By the method of the invention a substantially colorless sulfhydryl-terminated product of improved purity is obtained at an increased rate in the reaction of hydrogen sulfide and an allene compound. Subsequent polymerization of the crude product with a polyunsaturated olefin and/or an acetylene provides a substantially colorless sulfhydryl-terminated polythioether of the type in demand as a base polymer for sealants.

2. Description of the Prior Art

The ultraviolet light-initiated free-radical liquid phase addition of hydrogen sulfide to allene compounds (i.e. compounds containing the allene linkage, $>C=C=C<$) is known to produce sulfhydryl-terminated compounds i.e. dithiols and sulfhydryl-terminated thioethers. U.S. Pat. No. 3,488,270, to Griesbaum et al., discloses the liquid phase addition of hydrogen sulfide to allene initiated with ultraviolet light. The reaction is conducted in quartz which transmits high energy ultraviolet light, i.e. ultraviolet light of wavelength below 2600 Angstroms, as well as low energy, long wavelength ultraviolet light, i.e. ultraviolet light of wavelength of about 2600 to 3800 Angstroms. The crude reaction mixture is yellow and is usually contaminated with elemental sulfur. The formation of sulfur is accompanied by hydrogen gas evolution which may produce sufficient pressure to burst the reaction vessel. It has not been found feasible by conventional purification techniques, e.g. distillation, to remove the discoloration. This disadvantage is particularly serious since the principal reaction product, 1,3-propane dithiol, is (via polymerization with an unsaturated hydrocarbon) the precursor of sulfhydryl-terminated polythioethers which cure to valuable architectural sealants. Thus, when the discolored dithiol is reacted with an acetylenically and/or polyethylenically unsaturated compound in the presence of ultraviolet light as initiator according to known techniques (see U.S. Pat. Nos. 3,592,798 and 3,717,618 to Oswald and coassigned U.S. Ser. No. 501,716, filed Aug. 29, 1974, entitled "Polythioether Sealant Compositions" to B. F. Dannels), the sulfhydryl-terminated polythioether obtained is also discolored, and of unsatisfactory curing characteristics and, hence, is commercially unacceptable. Moreover the propanedithiol product must be recovered e.g. by fractional distillation, of the crude reaction mixture, if polymerization of the dithiol with the unsaturate is to be achieved. Apparently in the prior art allene-hydrogen sulfide reaction a side product is formed which inhibits the polymerization. In addition to the propanedithiol the crude reaction mixture contains about 30–50 weight percent sulfhydryl-terminated hydrocarbons with one, two, three, four or more thioether linkages, conveniently designated sulfhydryl-terminated thioether oligomers. These thioethers, because of the presence of terminal sulfhydryl substituents, would reasonably be expected to condense with the unsaturated reactant in the polymerization. However, because of the necessity to recover the propane dithiol from the crude reaction mass these sulfhydryl-thioether reactants are unavoidably lost, i.e. because of their relatively high boiling points, they cannot be readily recovered by distillation for use in the polymerization.

In coassigned U.S. Ser. No. 535,631, filed Dec. 23, 1974 entitled "Improved Method for Production of Sulfhydryl Compounds" to B. F. Dannels and E. J. Geering, filed of even date herewith, an improved method of reacting an allene compound, such as allene, and hydrogen sulfide is disclosed whereby the problem of yellow color and sulfur and hydrogen formation associated with the prior art reaction of an allene and hydrogen sulfide is overcome. According to the latter application, the pertinent technology of which is incorporated herein by reference, initiation of the reaction with ultraviolet light of wavelength substantially above about 2600 Angstroms, provides a substantially colorless reaction mixture free of sulfur. However in order to obtain a dithiol polymerizable with the unsaturated reactant, the reaction mixture of the latter improved process must also be subjected to a costly, tedious dithiol recovery step which involves loss of the valuable sulfhydryl-terminated thioether oligomers.

U.S. Pat. No. 2,398,481 and 2,411,983 to W. E. Vaughan et al. and U.S. Pat. No. 2,873,239 to W. R. Nummy et al. disclose liquid phase addition of hydrogen sulfide to unsaturated olefins in the presence of ultraviolet light of wavelength above 2900 Angstroms and of photosensitizing compounds. The reference processes, however, do not relate to reaction of olefins having the distinctive allene unsaturated group, i.e. two carbon-to-carbon double bonds attached to the same carbon atom and, hence, do not serve to remedy the problems encountered in the aforementioned prior art reaction of an allene and hydrogen sulfide.

SUMMARY OF THE INVENTION

The invention relates to a novel improvement in the preparation of a sulfhydryl-terminated compound by reaction of an allene compound with hydrogen sulfide which improvement comprises carrying out the reaction in the presence of ultraviolet light of wavelength substantially above about 2600 Angstroms and of a photosensitizing amount of an organic photosensitizing reagent for the reaction whereby the speed of the reaction is increased and a substantially colorless product of improved purity is obtained.

The allene compound employed is either allene or a substituted allene. When allene is the reactant the principal sulfhydryl-terminated product is 1,3-propane dithiol. When a substituted allene is the reactant, the principal product is generally the corresponding substituted 1,3-propanedithiol and/or substituted 1,2-propanedithiol.

In a preferred embodiment of the invention the crude colorless reaction mixture is polymerized with an acetylenically or polyethylenically unsaturated compound to obtain a substantially colorless sulfhydryl-terminated polythioether which is curable by known techniques to a valuable elastomeric polythioether useful as a sealant. The latter polymerization is preferably conducted in the presence of ultraviolet light of wavelength substantially above 2600 Angstroms. Preferably also, the polymerization is carried out in the presence of a photosensitizing amount of an organic photosensitizing reagent.

It was surprising to discover that use of the photosensitizing reagent and ultraviolet light of the described long wavelengths, i.e. of lower energy than the ultraviolet light containing wavelengths below 2600 Angstroms used in the prior art, would effectively initiate and increase the rate of the reaction of the allene compound and hydrogen sulfide, avoid hydrogen evolution and provide a crude product devoid of undesirable color and elemental sulfur. Unexpectedly also the use of long wavelength ultraviolet light and photosensitizing reagent in the reaction of the allene compound and hydrogen sulfide provides a crude reaction mixture which can be directly polymerized with unsaturated compounds without recovery of the dithiol, which costly step is required with dithiols prepared by prior art techniques. In other words, the present procedure eliminates that impurity or impurities which prevent the prior art crude reaction mixture from being polymerized and thereby permits the polymerization of sulfhydryl-terminated thioethers and thioether oligomers which constitute about 30 to 50 percent of the crude reaction mixture. The elimination of elemental sulfur and hydrogen formation in the reaction of the allene compound and hydrogen sulfide by the present improved procedure is also highly beneficial. The sulfur and hydrogen-forming reaction consumes hydrogen sulfide values charged to the reaction and hydrogen evolution may produce dangerously high pressure in the reaction vessel.

DETAILED DESCRIPTION OF THE INVENTION AND PREFERRED EMBODIMENTS THEREOF

The reaction of the allene compound and hydrogen sulfide is carried out substantially in accord with prior art reaction techniques except that a photosensitizing reagent is charged to the reaction and the ultraviolet light incident on the reaction mixture is filtered to exclude ultraviolet light of short wavelength, i.e. avelengths of about 100 to about 2600 Angstroms.

Generally ultraviolet light of the desired wavelength above 2600 Angstroms can be obtained by filtering broad spectrum ultraviolet light, i.e. of wavelength of about 100–3800 Angstroms, through a vitreous material which is transparent to ultraviolet of the desired wavelengths but is opaque to ultraviolet light of wavelengths of about 100–2600 Angstroms. Suitable vitreous filtering materials for use in the invention include glasses such as the proprietary glass compositions manufactured by the Corning Glass Co., for example, Corex (No. 9700), Corex D. Chemical Pyrex; (No. 7740) and Nonex (No. 7720) as well as lead glass and soda lime glass. Corex (No. 9700) which transmits ultraviolet light of wavelengths above about 2600 Angstroms and Chemical Pyrex which transmits ultraviolet light above about 2800 Angstroms are preferred filtering materials for obtaining ultraviolet light of the desired long wavelengths. The preferred materials contain 80–81% $SiO_2$, 13% $B_2O_3$, 4–5% $Na_2O$ and 2% $Al_2O_3$. The ultraviolet transmission characteristics of various glasses (at 1 m.m. thickness) suitable for use in the invention are compared with those of glasses, e.g. quartz and Vycor (No. 7910), which transmit undesirable short wavelength ultraviolet light in the section entitled "Transmission Characteristics of Quartz and Various Glasses" of "The General Electric Fused Quartz Catalog", Q-3, General Electric Co., 1952, the pertinent technology of which is incorporated herein by reference.

The photosensitizing reagent employed in the present process is a member of a known Michter'of organic aliphatic and aromatic hydrocarbons and substituted derivatives thereof which are capable of facilitating intermolecular energy transfer in light initiated chemical reactions. Generally the photosensitizer should be capable of absorbing light of the wavelength employed in the present reaction. Usually photosensitizing reagents contain one or more carbonyl substituents, e.g. keto or aldehyde groups, or thiocarbonyl substituents, e.g. thioketo groups, advantageously attached to one or more aryl substituents, e.g. phenyl or naphthyl groups. The photosensitizing reagents may also be further substituted with conventional substituents such a ether groups, halogen, e.g. chlorine and bromine, cyano, straight and branched chain lower alkyl and alkoxy groups i.e. alkyl and alkoxy substituents of one to six carbon atoms and primary, secondary, and tertiary lower alkyl or aryl amino groups. Typical sensitizing reagents for use in general in the present invention include aryl photosensitizers such as benzaldehyde, o-, m- and p-tolualdehyde, p-methoxybenzaldehyde, acetophenone, Michler's Ketone, Michler's thioketone, acetophenone, propiophenone, 1,3,5-triacetylbenzene, isobutyrophenone, triphenylmethyl phenyl ketone, diphenylene oxide, dibenzothiophene, o-dibenzoyl benzene, benzophenone, 4.4'-dichlorobenzophenone, p-diacetyl benzene, dinaphthalene, fluorene, 9-benzoylfluorene, p-cyanobenzophenone, 4,4'-bis(dimethylamino) benzophenone, ethyl phenylglyoxalate, alpha-naphthyl phenyl ketone, pyrene, benzil and the like.

Aliphatic photosensitizers include 2,3 butanedione, 2,3 pentanedione, acetone, acetaldehyde, methyl isopropyl ketone, propionaldehyde, isobutyroaldehyde as well as acyl halides such as acetyl bromide and propionyl bromide. Mixtures of these and equivalent photosensitizers including the isomers and homologs thereof may also be employed as the photosensitizing reagent in the present process.

Preferred photosensitizing reagents are those containing carbonyl substituents. Aryl photosensitizers are generally preferred over aliphatic photosensitizers. Especially preferred as photosensitizing reagents in the present invention are phenyl carbonyl compounds, i.e. photosensitizers containing a phenyl or substituted phenyl group attached to th carbonyl substituent. Benzaldehyde and acetophenone give an especially good result when employed as the photosensitizing reagent in the present process.

The allene compound utilized as reactant with hydrogen sulfide according to the invention is distinguished from ordinary olefins, such as ethylene, propylene and the like, in having two carbon-to-carbon double bonds attached to the same carbon atom. Allene compounds for use in general in the invention correspond to the general formula

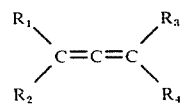

wherein $R_1$, $R_2$, $R_3$ and $R_4$ independently represent hydrogen and hydrocarbon radicals of 1 to 20 carbon atoms. The hydrocarbon radicals can be saturated straight chain and branched chain alkyl radicals, cycloalkyl radicals, aryl radicals, aralkyl radicals and alkaryl radicals and $R_1$ and $R_3$, when alkyl, can be joined together to form a cycloaliphatic ring. The $R_1$, $R_2$, $R_3$ and $R_4$ radicals may be further substituted with inert substituents such as halogen, e.g. chlorine, bromine and fluorine, carbo-lower alkoxy, i.e. ester, substituents, carbonyl, e.g. keto substituents and the like.

Typical allenes reactants for use in general in the invention include the following representative compounds:

However, it is found that the presence of methylacetylene in the allene starting material in no way interferes with the beneficial excellent results obtained in the present process. Accordingly such allene can advantageously be used in the present process.

The reaction of hydrogen sulfide and the allene compound is carried out in the liquid phase, i.e. under sufficient pressure to maintain the hydrogen sulfide and

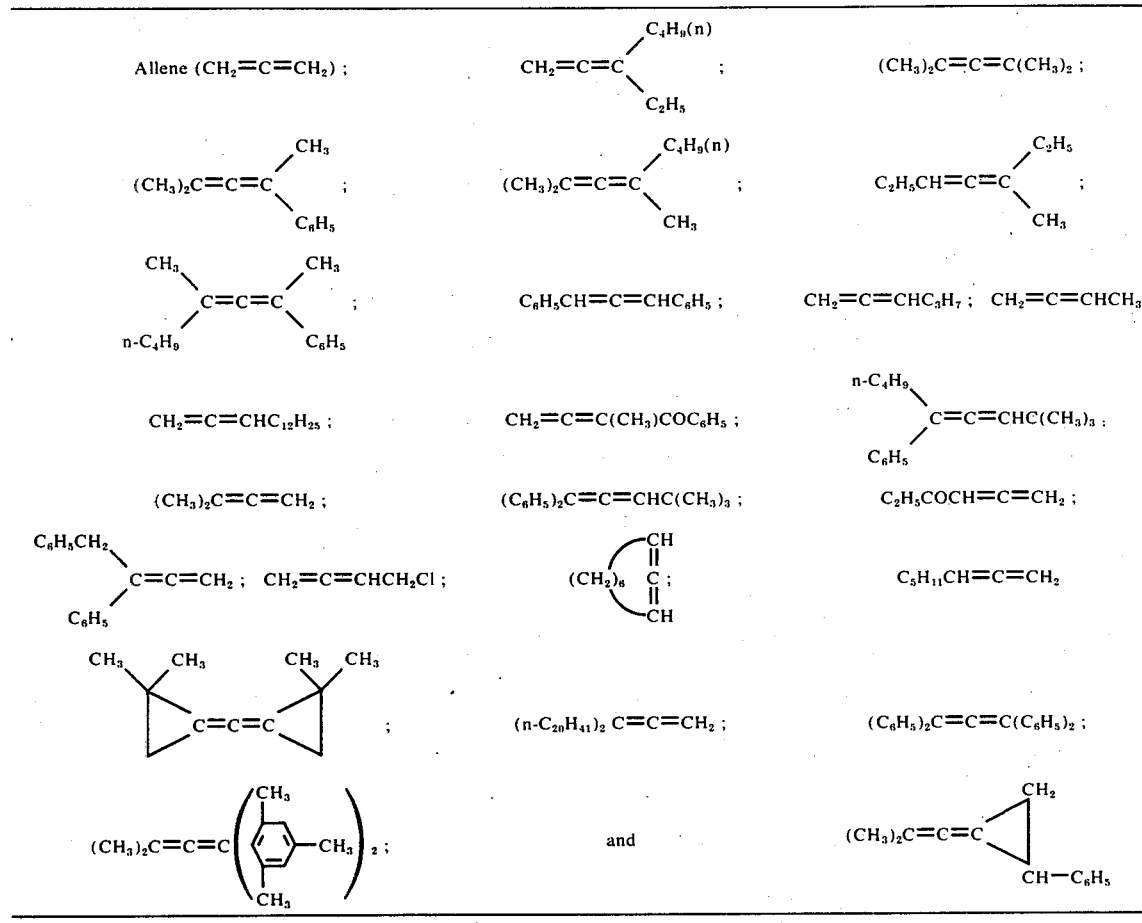

If desired, mixtures of these or of equivalent allene compounds including homologs or isomers thereof can be charged as the allene compound reactant.

All of the foregoing representaive compounds are known or are readily prepared by conventional synthetic techniques described in S. Patai, Ed. "The Chemistry of Alkenes", Interscience Publishers, 1964, pages 659–661, 762–3, 770, 1030–1060 and T. F. Rutledge, "Acetylenes and Allenes", Rheinhold Book Corporation, 1969, pages 4–31. The pertinent subject matter of these references is incorporated herein by reference.

Preferably the allene compound employment is a lower aliphatic allene, i.e. allene substituted with saturated alkyl groups of one to six carbon atoms or hydrogen. Preferably also can allene compound wherein the allene linkage is terminal, i.e. $R_3$ and $R_4$ are hydrogen in the above formula, is employed in the practice of the invention. Allene itself provides an especially good result. Frequently allene contains small amounts (up to about 0.5 to 10 mole percent) of methylacetylene which is also capable of reacting with hydrogen sulfide under the conditions of the present improved process.

organic reactants and products in the liquid phase. In general the reaction may be effected at temperatures in the range of about −100° to about +95° C. at reaction pressures ranging from about atmospheric (0 p.s.i.g.) to about 3000 p.s.i.g. Preferably the reaction is carried out at about −70° C to about +90° C, at pressures ranging from employed to about 1300 p.s.i.g., especially at about −20° C to about 70° C. at pressures of about 60 to about 400 p.s.i.g.). If desired, the reaction can be carried out efficiently at low pressures ranging from about atmospheric pressure to about 60 p.s.i.g. at reaction temperatures of about −70° to −40° C.

The reaction of the hydrogen sulfide with the allene compound is exothermic. The temperature in the reaction vessel can be conveniently controlled by conventional cooling techniques. For example a cooling cil can be disposed within the reaction mixture and or a cooling jacket can surround the reaction vessel. Also streams of air or nitrogen flowed along the outside walls of the vessel are useful in cooling the reaction vessel or for removing the heat which is generated by the ultraviolet light source.

The source of ultraviolet light employed in carrying out the present process include sunlight, a carbon arc, a mercury vapor lamp, a tungsten arc or Kronmeyer lamp. Advantageously, the light source is disposed outside the reaction vessel which is constructed of the vitreous material employed in the invention to filter the ultraviolet light. Alternatively there is used a reaction vessel which is constructed predominantly of stainless steel, glass lined stainless steel or other light-opaque material inert to the reactants and products of the present process but which contains a window or, advantageously, a light well, constructed of the vitreous, ultraviolet filtering material. If desired a quartz well equipped with a removable filter insert of the desired vitreous material is used. When a reaction vessel containing a light well is employed, the ultraviolet light source, advantageously a mercury vapor lamp, is disposed within the well during the reaction. As will be apparent to those skilled in the art the reaction vessel used should be capable of withstanding superatmospheric pressure when such pressure is employed in carrying out the reaction.

The organic photo-sensitizing reagent employed in the present improved process is charged to the reaction of the allene compound and hydrogen sulfide in a small aount sufficient to sensitize the reaction toward the ultraviolet light employed as initiator, generally 0.0005% to about 5% based on the weight of the reaction mass. Preferably, the photo-sensitizing reagent is charged in an amount of about 0.001% to 2%, and especially about 0.1 to 1% based on the weight of the reaction mixture.

The photo-sensitizing reagent (or derivative(s) thereof in the event it is decomposed by ultraviolet light or reacts with the hydrogen sulfide) will remain in the crude reaction mixture when the latter is subjected to polymerization according to a preferred embodiment of the invention. However the resultant presence of the photo-sensitizer or residues thereof in the sulfhydryl terminated polythioether usually has no deleterious effect on the chemical or physical properties of the polymer or the cured elastomer prepared therefrom.

In the present improved process the molar proportion of hydrogen sulfide to the allene compound employed can be from about 1:1 to about 20:1 and is preferably about 1.5:1 to about 15:1.

An especially good result is obtained in the present process employing hydrogen sulfide and the allene compound in molar ratio of about 2.0:1 to 12:1.

The crude reaction mixture obtained by reaction of the allene compound and hydrogen sulfide acccording to the invention is substantially colorless and devoid of elemental sulfur. The crude reaction mass is admixed, desirably without recovery of the dithiol, with an unsaturated reactant e.g. methyl acetylene, and 1,2,4-trivinyl cyclohexane, for polymerization to a sulfhydryl-terminated polythioether according to a preferred embodiment of the invention.

The crude reaction mixture obtained from the reaction of hydrogen sulfide and allene in accordance with the invention is advantageously stripped of volatiles, such as allylmercaptan and dissolved hydrogen sulfide, by moderate heating, say at 90°–110° Centigrade, at diminished pressure, e.g. about 1 to 100 mm of mercury for about 0.5 to 1.5 hours. If desired, the propanedithiol or substituted propanedithiol can be readily recovered from the crude reaction mixture by a conventional purification technique, e.g. fractional distillation, advantageously at diminished pressure, of the crude reaction mixture. The reaction of hydrogen sulfide and allene compound can be carried out in an appropriate conventional inert solvent e.g. benzene, but is preferably effected in bulk to facilitate the direct utilization of the crude reaction mixture as described above or to facilitate the recovery of the dithiol product.

In a preferred embodiment of the invention the propanedithiol product of the allene compound — hydrogen sulfide reaction or, advantageously, the crude reaction mixture containing the dithiol as predominant product is polymerized with an unsaturated organic compound to provide a substantially colorless high molecular weight sulfhydryl-terminated polythioether capable of being cured to a substantially colorless elastomeric sealant.

The polymerization reaction proceeds by a free radical mechanism and can be initiated by conventional means such as cumene hydroperoxide, tertiary butyl hydroperioxide, bis-azo-isobutyronitrile, azo-bisvaleronitrile, gamma radiation and broad spectrum ultraviolet light, i.e. ultraviolet light of about 100–3800 Angstroms wavelength. Preferably, however, the polymerization reaction is initiated with ultraviolet light of wavelength substantially above about 2600 Angstroms i.e. low energy ultraviolet light of the type employed in the abovedescribed reaction of the allene compound and hydrogen sulfide.

Preferably the photoinitiated polymerization of the sulfhydryl-terminated product and the unsaturated compound is carried out in the presence of a photosensitizing amount of an organic photosensitizing reagent as in the above-described reaction of the allene compound and hydrogen sulfide. When the polymerization is effected in the presence of the photosensitizing reagent and ultraviolet light of wavelength substantially above about 2600 Angstroms, the colorless sulfhydryl-terminated polythioether is formed at an enhanced reaction rate and a polymer can be prepared of substantially higher molecular weight than in comparable polymerizations wherein the photosensitizing reagent is omitted and ultraviolet light containing short wavelengths, i.e. wavelength below 2600 Angstroms, is employed.

The unsaturated compound which is reacted with the sulfhydrylterminated product of the reaction of hydrogen sulfide and the allene compound is a hydrocarbon having at least one acetylenic bond or at least two ethylenic bonds. Olefins with one ethylenic bond react but do not give polymeric products. Generally the acetylenically unsaturated reactant will contain 2 to 50 carbon atoms and can be of mono-, di-, tri- or higher functionality, i.e. it can contain one, two, three or more unsaturated sites per molecule. The ethylenically unsaturated reactant will contain 3 to 50 carbon atoms and be of di, tri or higher functionality. If desired, a multifunctional unsaturated reactant containing both ethylenic and acetylenic unsaturation can be used. The unsaturated reactant may contain one or more halogen, e.g. fluorine, chlorine, and bromine, substituents attached either to a saturated or unsaturated carbon atom. Also the unsaturate may contain other conventional inert substituents such as ether groups, aryl substituents, such as phenyl, naphthyl and lower alkyl phenyl, cycloalkyl substituents such as cyclopentyl, cyclohexyl and cyclododecyl and ester groups, i.e. carboxy-lower alkyl groups such as carboxy methyl. Cyclic, straight-chain and branched chain unsaturated compounds can be employed in the polymerization reaction.

Typical suitable unsaturated compounds for use in the invention include the following representative examples: allene and the above indicated substituted allenes, cyclohexadiene-1,3, 2-methylbutadiene-1,3,2,4-dimethylhexadiene-2,4, butadiene-1,3, pentadiene-1,3, pentadiene-1,4,hexadiene-1,4, hexadiene-1,5, acetylene, methyl acetylene, butyne-1, butyne-2, bis(pentacosyl)acetylene pentyne-2, hexyne-1, cetyne-1, octylacetylene, phenylacetylene, cyclopentadiene, 1,3,5-hexatriene, cyclopentyl-acetylene, vinyl cyclohexene, 1,2,4-trivinyl cyclohexane, 1,3,5-trivinyl cyclohexane, p-divinyl benzene, sym.-trivinyl benzene, unsaturated organic halides, such as perfluorobutadiene-1,3, 2-chloromethyl butadiene-1,3, 2-bromomethyl pentadiene-1,3, and perfluoro propyne-1, and unsaturated organic ethers such as divinyl ether, diallyl ether, dimethallyl ether as well as the homologs and isomers of such compounds. Mixtures of two or more of the above listed unsaturated compounds can be charged to the polymerization also.

Preferred unsaturated reactants of the invention contain up to 12 carbon atoms. In order to obtain an elastomer of desirable mechanical properties for sealant applications, the unsaturated reactant is preferably predominantly an acetylenically unsaturated hydrocarbon, most preferably a monoacetylenically unsaturated compound and especially an aliphatic acetylene containing the unsaturation solely in the alpha or terminal position. Use of a preferably aliphatic terminally unsaturated acetylene, e.g. methyl acetylene, provides an especially good result. In order to provide desirable chain branching in the -sulfhydryl-terminated polythioether product, the unsaturated reactant also advantageously contains a minor amount of a trifunctional unsaturated hydrocarbon, especially an ethylenically unsaturated hydrocarbon, e.g. 1,2,4-trivinyl cyclohexane.

The polymerization reaction can be carried out at temperatures of about $-100°$ C to $+175°$ C, preferably about $0°$ to $70°$ C., at pressures ranging from about 1 to about 10 atmospheres, preferably from about 1 to 5 atmospheres. The reaction can be effected wholly in the liquid phase, if desired, employing sufficient pressure to maintain the reaction constituents in the liquid state. However, when the unsaturated reactant is a gas at the particular reaction temperature used, it is advantageous to bubble or sparge the unsaturated reactant into the liquid reaction mass maintained at atmospheric pressure.

The molar ratio of unsaturated reactant(s) to sulfhydryl-terminated reactant charged to the polymerization reaction is generally about 0.7:1 to about 0.999:1. Molar ratios of unsaturated reactant to sulfhydryl-terminated reactant of exactly 1:1 or greater can be used but are desirably avoided since such ratios provide polythioethers which terminate in unsaturated groups rather than in sulfhydryl substituents. Preferably the molar ratio of unsaturated compound(s) to sulfhydryl-terminated reactant is about 0.85 to about 0.99.

When, in accordance with an especially preferred embodiment of the invention, the unsaturated reactant contains a monofunctional acetylenic compound together with a small amount of tri-unsaturated compound, so as to effect desirable chain branching in the product, the proportion of trifunctional unsaturated compound charged is about 0.0005 to 0.05, preferably about 0.005 to 0.03 moles per mole of the sulfhydryl-terminated reactant.

The polymerization reaction, when light-initiated, is carried out in reaction equipment substantially similar to that employed in carrying out the reaction of hydrogen sulfide and the allene compound. When the crude reaction mixture of the hydrogen sulfide-allene compound reaction is used directly as the sulfhydryl reactant in the polymerization, advantageously the same reaction vessel may be employed for both reactions.

The polymerization reaction can be carried out in a conventional inert solvent or in an appropriate conventional water-surfactant emulsion system. Preferably the polymerization is conducted in bulk which facilitates recovery of the polythioether product without further purification steps. The sulfhydryl-terminated polythioether product is fluid and can be flowed or decanted from the reaction vessel on completion of the reaction.

The crude sulfhydryl-terminated polythioether product is advantageously stripped of volatiles, e.g. low molecular weight cyclic polythioethers, which have an unpleasant odor, by heating the polymer product at about $170°-200°$ Centigrade under a diminished pressure of about 0.001 to 5 mm. of mercury, for about 0.5 to 5 hours. Alternatively the low molecular weight cyclic polythioethers can be removed by conventional steam distillation techniques.

The polymerization according to the invention is generally accomplished in a relatively short period i.e. the polymerization mass attains maximum viscosity, indicative of maximum polymer molecular weight, within a period of only about 1 to 15 hours.

The sulfhydryl-terminated polythioether which is recovered from the polymerization reaction of the invention is substantially colorless and hence of enhanced commercial value. These polythioethers are important as reactive precursors, i.e. prepolymers, of architectural sealant elastomers, since they can be cross-linked to elastomeric three-dimensional networks using a variety of known curing techniques. Advantageously the present sulfhydryl-terminated polythioethers can be cured by mixing about 1 to 20 grams per 100 grams of polythioether of an oxidizing agent such as lead dioxide, manganese dioxide, and calcium peroxide and allowing the mixture to cure at room temperature.

As another example of curing methods, sulfhydryl-terminated polythioethers are treated with epoxides having at least 2 epoxide groups per molecule in the presence of a base catalyst usually an amine. For example, 1.2 mole equivalent of a bis-phenol-A-diglycydyl ether resin is reacted with 1.0 mole equivalent of a sulfhydryl-terminated polythioether in the presence of 5 wt. percent amine catalyst, i.e. tri-2,4,6-(dimethylaminomethyl)phenol. Chain extension takes place at room temperature due to the sulfhydryl-epoxide reaction. The cure is completed in 2 hours at $100°$ due to the reaction of the hydroxy groups formed with the excess epoxide.

Sulfhydryl-terminated polythioethers undergo similar amine catalyzed reactions with diepisulfides. These reactions, however, do not require heating for complete cures, since chain extension and crosslinking both occur under mild conditions.

Alternatively, the sulfhydryl-terminated polythioethers can be cured with about equimolar amounts or an excess of a diisocyanate to produce polythiourethanes.

Also the sulfhydryl-terminated polythioethers can be cured by reaction with an organic peroxy compound such as an organic peroxide or organic perester, especially tertiary butyl perbenzoate.

In using the sulfhydryl-terminated polythioethers as sealants, various conventional adjuvants are normally added to the polythioether prior to initiation of the curing operation, for example stabilizers, plasticizers and various types of fillers. Typically carbon fillers such as carbon black, channel black, furnace or petroleum coke can be incorporated into the sulfhydryl-terminated polythioether in amounts up to about 200 parts filler per 100 parts by weight of polythioether. Mineral fillers can be used also including the usual non-carbon fillers or pigments such as titanium dioxide or the oxides, hydroxides, sulfides, carbonates, etc. of silicon, aluminum, magnesium, zinc, calcium, barium or the like, as well as the silicates or aluminates of the various metals indicated above. The production and curing of polythioether elastomeric sealant compositions from sulfhydryl-terminated polythioethers is more particularly described in aforementioned U.S. application Ser. No. 501,716, the pertinent technology of which is incorporated herein by reference.

The present sulfhydryl-terminated polythioethers are capable of be cured. in situ at room temperature to thioether elastomers of excellent tensile strength and elasticity. Moreover, the resultant elastomers are resistant to degradation by oxygen, ozone and organic solvents. Accordingly the present elastomers are especially useful in sealant applications, for example for filling and sealing joints, and seams in many areas of construction including insulated glass windows, floors and pavements. A particular advantage of the present sulfhydryl-terminated polythioethers in such architectural sealant applications is their substantial lack of color. Thus, the present substantially colorless sulfhydryl-terminated polythioether products can be cured. by a white or colorless curing agent, e.g. calcium peroxide, to provide an attractive seal devoid of discoloration.

In addition to the foregoing commercial applications, the elastomers and rubbers prepared by curing the sulfhydryl-terminated polythioethers can also be employed as printing rollers and gaskets.

The following examples serve to illustrate the various aspects of the invention but are not intended to limit it. Where not otherwise noted throughout this specification and claims, parts, percentages and proportions are by weight and temperatures are in degrees centigrade.

EXAMPLE 1

A 1.5 gallon steel glass-lined pressure vessel with a nickel head and a 55 mm. outside diameter quartz light well is equipped with pressure sensors, a thermocouple and a Chemical Pyrex (7750 Pyrex manufactured by the Corning Glass Co.) filter inserted in the light well. A 450 watt medium pressure mercury vapor arc (Hanovia Model 679A-36 ultraviolet lamp) is placed within the light well through which nitrogen gas coolant is circulated. The reaction vessel is cooled to about −20° in a refrigerated aqueous ethylene glycol bath. Hydrogen sulfide and allene in a molar ratio of about 10.5:1 and about one gram (0.0094 mole corresponding to about 0.03% based on the weight of the reaction mixture) of benzaldehyde are charged to the vessel which is sealed.

The mercury vapor lamp is switched on and allowed to irradiate the reaction mass for about 7 hours during which the reaction temperature is between about −20° and +3° and the reaction pressure is about 110 to 210 p.s.i.g. The reaction vessel is then vented to a receiver at atmospheric pressure which is cooled to about −60° in a dry ice-acetone bath in order to recover hydrogen sulfide and any unreacted allene. There is thus obtained 1843 grams (corresponding to about 97% conversion based on allene) of a clear colorless crude reaction mixture which is stripped of volatiles, e.g. residual hydrogen sulfide and traces of allyl mercaptan, by heating for one hour at about 100° under a diminished pressure of about 25 mm. of mercury. The resultant crude colorless reaction mass is predominantly 1,3-propanedithiol with minor amounts i.e. about 30 to 50% of sulfhydryl-terminated monothioether, sulfhydryl-terminated polythioether oligomers and 1,2-propanedithiol.

A substantially similar excellent clear colorless crude reaction mixture containing 1,3-propane dithiol as predominant product can be obtained by replacing the Pyrex light well filter in the above reaction with one of Corex (9700 Corex manufactured by the Corning Glass Co.). A similar excellent crude product is also obtained when the benzaldehyde is replaced by acetophenone or benzophenone.

The composition of 7740 Pyrex glass is 81% $SiO_2$, 13% $B_2O_3$, 4% $Na_2O$, and 2% $Al_2O_3$.

The composition of 9700 Corex glass is 80% $SiO_2$, 13% $B_2O_3$, 5% $Na_2O$ and 2% $Al_2O_3$.

EXAMPLE 2

A 0.5 liter Chemical Pyrex round bottomed flask fitted with a stirrer, thermometer, gas inlet tube and dry ice reflux condenser is flushed with nitrogen and charged with a vacuum stripped crude reaction mixture (108 grams, about one mole, computed as 1,3 propanedithiol) prepared by a procedure substantially similar to that of Example 1 and 0.81 grams (0.005 mole) of 1,2,4 trivinylcyclohexane. A 100 watt medium pressure mercury arc lamp of the type employed in Example 1 positioned horizontally 1/2 inch beneath the flask is allowed to illuminate the stirred reaction mixture for 30 minutes. The reaction mass is then saturated with methyl acetylene charged through the gas inlet tube beneath the surface of the reaction mass which is maintained at a temperature of about 21°-53° at atmospheric pressure. The methyl acetylene addition is continued at a rate sufficient to maintain slight reflux in the reaction mixture. After 6 hours 34.7 grams (0.866 mole) of methyl acetylene has reacted. The liquid sulfhydryl-terminated polythioether (143.5 grams) is poured from the reaction flask and heated at about 200° under a diminished pressure of about 0.5 mm mercury for about one hour to strip off any volatiles such as low molecular weight cyclic polythioethers. The vacuum stripped liquid polymer has a viscosity of 2080 poises indicating a number average molecular weight of about 8000.

The sulfhydryl-terminated polythioether is substantially clear and colorless. It is cured at room temperature with lead dioxide (7.5 parts per hundred parts of sulfhydryl-terminated polythioether) in substantial accord with the procedure of aforementioned U.S. application Ser. No. 501,716. The resultant cured polythioether elastomer has a tensile strength of 46 pounds per square inch and a good elongation of 528%.

A colorless, cured polythioether elastomer of similar good mechanical properties is obtained by curing the sulfhydryl-terminated polythioether with a white or colorless curing agent such as calcium peroxide.

EXAMPLES 3–6

In Examples 3–6 summarized in the table below the procedure of Example 1 is repeated substantially as described except that the molar ratio of hydrogen sulfide to allene is varied slightly as shown, the amount of photosensitizing reagent charged is varied from 0 to 4 grams as shown and after the initial first hour of reaction, a sample of the reaction mixture is removed. After removal of unreacted hydrogen sulfide and allene by evaporation, the sample is weighed to determine the percent conversion of allene and the weight of the crude reaction product formed in the first hour of reaction.

EXAMPLE 7 (Control)

Part A

The procedure of Example 1 is repeated substantially as described employing a molar ratio of hydrogen sulfide to allene of 8.3:1 and omitting the addition of the benzaldehyde. After a reaction period of 14 hours there is obtained 1790 grams (corresponding to about 100% of the allene) of clear, colorless liquid reaction mixture devoid of any suspended or precipitated solid. After being stripped of volatiles by heating under diminished pressure the crude reaction mixture is subjected to analysis by gas-liquid chromatography which indicates the presence of about 68.7 percent of propanedithiol (of which no more than 5 percent is 1,2-propanedithiol, the remainder being 1,3-

TABLE

| Example | Grams of Benzaldehyde Photo-sensitizer Charged | Molar Ratio of Hydrogen sulfide to Allene | % Conversion of Allene Reactant in First Hour | Grams Crude Reaction Product Recovered After One Hour Reaction |
| --- | --- | --- | --- | --- |
| 3(Control) | 0 | 11.2:1 | 20 | 160 |
| 4 | 1 (0.03%) | 11.1 | 50 | 400 |
| 5 | 2 (0.06%) | 11.2:1 | 60 | 485 |
| 6 | 4 (0.12%) | 9.8:1 | 80 | 650 |

The crude reaction mixtures of Examples 3–6 are treated with methylacetylene and 1,2,4 trivinylcyclohexane in substantial accord with the procedure of Example 2. The crude of control Example 3 fails to react. However the crudes of Examples 4–6, which are clear and substantially colorless, polymerize to excellent clear, substantially colorless sulfhydryl-terminated polythioethers.

The sulfhydryl-terminated polythioethers obtained from the crude reaction products of Examples 5 and 6 are cured with lead dioxide substantially as described in Example 2. The resultant polythioether elastomer derived from the Example 5 crude has a tensile strength of 142 lbs. per in.$^2$, an elongation of 585% and a hardness of 34 Shore Durometer units (A scale).

The cured elastomer derived from the Example 6 crude has a tensile strength of 110 lbs. per in.$^2$, an elongation of 850% and a hardness of 30 Shore Durometer units (A scale).

The sulfhydryl-terminated polythioether products derived from the crude reaction mixtures of Examples 4–6, when cured with a colorless or white curing agent such as calcium peroxide, provide attractive substantially colorless polythioether elastomers, having good mechanical properties, substantially equivalent to those of the lead dioxide-cured elastomers described above.

Substantially similar results are obtained when the procedure of Examples 3–6 is repeated replacing the benzaldehyde photosensitizing reagent with acetophenone.

From comparison of the results of Examples 4–6 with those of control Example 3, it is apparent that use of an organic photosensitizing reagent together with initiation by ultraviolet light of long wave lengths as taught by the invention not only increases the speed of the reaction of hydrogen sulfide and the allene compound but also provides a crude reaction product which, without further purification is capable of undergoing polymerization with an unsaturated monomer such as methylacetylene and 1,2,4-trivinylcyclohexane.

propanedithiol) with the remaining portion of the crude reaction mixture being a mixture of sulfhydryl-terminated oligomers containing 1,2 or more thioether linkages per molecule. Fractional distillation of the crude reaction mixture through a packed column (16 inch length) provides a colorless fraction, b.p. 87–89/46 mm of mercury, amounting to about 50% of the distillation charge which is identified as crude 1,3-propanedithiol. The distillation residue is also colorless.

Substantially similar clear, colorless crude 1,3-propanedithiol can be obtained by replacing the Pyrex light well insert in the above reaction with one of Corex.

The recovered distilled propanedithiol is treated with methylacetylene and 1,2,4-trivinylcyclohexane substantially in accord with the reaction technique of Example 2. There is obtained after about a five hour reaction period a substantially clear colorless sulfhydryl-terminated polythioether which, when stripped of volatiles, has a viscosity of about 2000 poises indicating a molecular weight of about 10,000.

Part B

The procedure of Part A is carried out substantially as described except that the fractional distillation of the propanedithiol is omitted and the vacuum stripped crude is charged directly to the polymerization. No reaction of the crude reaction mixture with the methylacetylene and 1,2,4-trivinylcyclohexane is obtained.

Part C

The procedure of Part A is repeated substantially as described except that the polymerization is carried out in a flask of Vycor (7910 Vycor glass manufactured by the Corning Glass Co.) which transmits to the reaction ulraviolet light containing wave lengths below about 2600 Angstroms. The reaction is carried out for 10 hours. The liquid sulfhydryl-terminated polythioether product is cloudy but substantially colorless. The product, after removal of volatiles under diminished pressure, has a viscosity of 348.75 poises and a molecular weight of 1940.

An intractable gelled material is found adhering to the walls of the reaction flask after removal of the sulfhydryl-terminated polythioether. While the gelled material is in the main colorless, that portion on the flask wall nearest the ultraviolet source has brown discoloration.

Part D

The procedure of Part A is repeated substantially as described except that the colorless distillation residue of the fractional distillation rather than the propanedithiol distillate is charged to the polymerization. No reaction between the distillation residue and the methylacetylene and 1,2,4-trivinylcyclohexane occurs.

Comparison of the results of Example 7, Parts A-C and those of Examples 1 and 2 indicates that omission of the organic photosensitizing reagent from the reaction of hydrogen sulfide and the allene compound results in a crude reaction mixture which does not polymerize with the acetylenically and/or poly-ethylenically unsaturated reactant.

Comparison of the results of Part A with those of Part C indicates that use of ultraviolet light of wavelength substantially above 2600 Angstroms to initiate the polymerization reaction increases the rate of the polymerization and the molecular weight of the sulfhydryl-terminated polythioether product and avoids formation of the intractable gelled side product.

Comparison of the results of Part A with those of Parts B and D indicate that polymerization inhibiting impurity or impurities which are formed when the photosensitizing reagent is omitted from the reaction of the allene compound and hydrogen sulfide is apparently removed in the distillation residue when the crude reaction mixture is fractionally distilled to recover the propane dithiol.

EXAMPLE 8 (Control)

Part A

The procedure of Example 1 is repeated substantially as described except that the molar ratio of hydrogen sulfide to allene is about 8.7:1 and the benzaldehyde photosensitizer and the Chemical Pyrex filter insert is omitted so that the quartz light well transmits to the reaction mixture ultraviolet light of wavelengths below about 2600 Angstroms as well as wavelengths of ultraviolet light up to about 3800 Angstroms. After the reaction has proceeded for 11.2 hours, there is obtained 1213 grams (corresponding to a 72% conversion of allene) of crude reaction mixture which is yellow and cloudy indicating the presence of suspended solid, which is identified as sulfur. Analysis of the vacuum stripped reaction mass indicates the presence of about 58 weight percent of propanedithiol. Fractional distillation of the reaction mixture provides a 46% recovery (based on the distillation charge) of a 1,3-propanedithiol fraction, b.p. 84–87 at 39 mm. of mercury, which is yellow but clear of suspended sulfur. Neither refractionation nor adsorption treatment, (on a vertical column filled with particulate absorbent alumina) remove the yellow color of the distilled 1,3-propanedithiol.

The discolored, distilled 1,3-propanedithiol is reacted with methylacetylene and 1,2,4-trivinylcyclohexane substantially in accord with the procedure of Example 2. The resultant sulfhydryl polythioether is yellow.

Part B

The above-described allene hydrogen sulfide reaction is repeated omitting the fractional distillation of the propanedithiol, i.e. the yellow, sulfur-containing crude reaction mixture is treated with methylacetylene and 1,2,4-trivinylcyclohexane substantially in accord with the procedure of Example 2. No polymerization occurs.

Results substantially similar to those of Parts A and B are obtained when a Vycor filter insert is disposed in the light well of the reaction vessel.

Comparison of the results of Example 8 with those of Examples 1 and 2 indicate that carrying out the reaction of the allene compound and hydrogen sulfide in presence of ultraviolet light containing wave lengths below about 2600 Angstroms and in the absence of the organic photosensitizing compound provides a crude reaction mixture which cannot be polymerized with the unsaturated reactant. Moreover, when the allene compound hydrogen sulfide reaction is carried out under the foregoing prior art conditions, the reaction mixture must be subjected to a purification step to recover a sulfhydryl-terminated hydrocarbon product i.e. the propanedithiol, which will polymerize with the unsaturated compound. Even with such recovery the objectionable yellow color of the recovered propane dithiol is transferred on polymerization of the dithiol to the sulfhydryl terminated polythioether.

EXAMPLE 9

A 1,3-propane dithiol-containing vacuum stripped crude reaction mixture (1257.2 grams, 11.6 moles computed as 1,3-propanedithiol) prepared substantially as described in Example 1 is polymerized at 40°–58° under atmospheric pressure with 9.43 grams (0.058 mole) of 1,2,4-trivinylcyclohexane and 372 grams (9.34 mole) of methylacetylene substantially as described in Example 2 except that the duration of reaction is 10.5 hours, the ultraviolet lamp is positioned 4 inches beneath the pyrex flask and the reaction is carried out in the presence of 2.33 grams (0.022 mole) of benzaldehyde. There is obtained as product 1641 grams of liquid, clear substantially colorless sulfhydryl-terminated polythioether. After being heated for 4 hours at about 200° under a diminished pressure of about 0.05 mm to remove volatiles, the product has a viscosity of 870 poises corresponding to a molecular weight of 5700. This product is cured to an excellent polythioether elastomer by a procedure substantially similar to that of Example 2.

Substantially similar excellent results are obtained when the above polymerization is repeated employing acetophenone in place of benzaldehyde.

The reaction of allene and hydrogen sulfide according to the procedure of Example 1 and the polymerization according to Example 9 can be carried out in the same reaction vessel, e.g. the glass lined pressure vessel of Example 1, by omitting the vacuum stripping of the crude reaction mixture of Example 1 and equipping the reaction vessel with a gas inlet tube for charging methylacetylene.

EXAMPLE 10

The reaction of allene and hydrogen sulfide is repeated substantially as described in Example 1 except that the molar ratio of hydrogen sulfide to allene is 2.46:1, the amount of benzaldehyde charged is 10g. (corresponding to about 0.32% based on the weight of the reaction mixture), the temperature of the refrigerated aqueous ethylene glycol bath is −60°, the reaction temperature is between about −50° and −60°, and the reaction pressure is between atmospheric pressure and about 40 p.s.i.g. After a reaction period of only 9.5 hours there is obtained 2260 grams (corresponding to about 98% conversion based on allene charged) of clear colorless crude reaction mixture containing 1,3 propanedithiol as predominant product.

EXAMPLE 11 (Control)

The procedure of Example 10 is repeated substantially as described except that the light well filter of chemical pyrex is replaced by one of Vycor (7910 Vycor) which transmits ultraviolet light of wavelength below 2600 Angstroms. After a reaction period of 11.2 hours there is obtained only 1987g.(corresponding to a conversion of only 86.8% based on allene charged) of the crude reaction mixture containing 1,3-propanedithiol as predominant product.

The substantially quantitative conversion of allene to crude product in Example 10 compared to the substantially lower conversion of allene in Example 11 which requires a longer reaction period than the reaction of Example 10 indicates that the photosensitized reaction of hydrogen sulfide and an allene compound initiated by ultraviolet light of wavelength substantially above about 2600 Angstroms is substantially more rapid than the corresponding photosensitized reaction initiated by ultraviolet light containing wavelengths below 2600 Angstroms.

The following Example 12 illustrates the use of the present sulfhydryl-terminated polythioether in a storage stable extrudable sealing composition containing calcium peroxide as curing agent and the cure thereof in the presence of atmospheric moisture at ambient temperature to obtain a white polythioether elastomer.

| Example 12 | | Parts |
| --- | --- | --- |
| Part A | Sulfhydryl-terminated polythioether (prepared substantially as described in Example 9) | 100 |
| | Multifex MM (Note 1) | 50 |
| | Duramite (Note 2) | 40 |
| | Titanium dioxide | 10 |
| | Santicizer 160 (Note 3) | 50 |
| | Tetraethyl thiuram disulfide | 0.4 |
| | 2-Mercaptoethanol | 0.88 |
| Part B | | |
| Paste I: | | |
| | Barium oxide | 15.6 |
| | HB-40 (Note 4) | 9.4 |
| Paste II: | | |
| | Calcium peroxide | 15 |
| | HB-40 | 14 |
| | Silane A-187 (Note 5) | 2.5 |
| | | 307.78 |

Notes:
(1) Multifex MM is ultrafine precipitated calcium carbonate manufactured by Diamond Alkali Co.
(2) Duramite is ground calcium carbonate manufactured by White Pigment Corp.
(3) Santicizer 160 is butyl benzyl phthalate plasticizer manufactured by Monsanto Co.
(4) HB-40 is a proprietary hydrogenated terphenyl manufactured by Monsanto Co.
(5) Silane A-187 is gamma glycidoxypropyl trimethoxy-silane manufactured by Union Carbide Corp.

At ambient temperature the ingredients of Part A are mixed together in three passes through a three roll mill. Paste I is prepared by mixing the listed ingredients thereof in three passes through a three roll mill. Paste II is prepared by mixing the listed ingredients thereof in three passes through a three roll mill. The Part A ingredients and Paste I are blended by mixing in a slow speed mixer for about 5 minutes under an inert atmosphere of dry nitrogen and the mixture is allowed to age by standing at room temperature for one hour under dry nitrogen. Paste II and the silane are then added and the mixture is agitated for about five minutes at ambient temperature under dry nitrogen in the slow speed mixer. The resultant paste is packed out in a collapsible aluminum tube with a screw top and then sealed. The tube is maintained at ambient temperature for 60 days during which it is periodically opened for testing the extrusion of the paste. After ageing for 3 days the viscosity of the paste remains constant and the paste is readily extrudible even after 60 days storage. When a sample of the paste is exposed to the atmosphere at 50% relative humidity at ambient temperature, the sample becomes tack-free in 3 days and cures to an attractive white polythioether elastomer in 2 weeks.

Samples of the sealant paste are extruded onto glass and aluminum, and cured substantially as described above for testing of peel strength in accord with the procedure of Federal Specification No. TTS-00227E (COM-NBS), National Bureau of Standards. After one week immersion in water at 25°, the cured elastomer samples on glass and aluminum have excellent peel strengths in the range of about 20–30 lbs. per in.

Substantially similar excellent results are obtained in the foregoing procedure when the above sealant composition is replaced by substantially similar sulfhydryl-terminated polythioether-containing formulations which contain barium peroxide or zinc peroxide as curing agent in place of calcium peroxide.

It is to be understood that the invention is not limited to the specific examples which have been offered merely as illustrative and that modifications can be made without departing from the spirit of the invention.

What is claimed is:
1. In the liquid phase reaction of an allene compound with hydrogen sulfide to prepare a sulfhydryl-terminated product, the improvement which comprises carrying out the reaction at a reaction temperature of about −100° to about 90° Centigrade, a reaction pressure of 0 to 3000 p.s.i.g. and a molar ratio of hydrogen sulfide to the allene compound of about 1:1 to about 20:1 in the presence of ultraviolet light of wavelength substantially above about 2600 Angstroms and a photosensitizing amount in the range of about 0.0005 to about 5% based on the weight of the reaction mixture of an organic photosensitizing reagent for said reaction whereby the speed of the reaction is increased and a substantially colorless product of improved purity is obtained.

2. The process of claim 1 wherein the allene compound is one wherein the allene linkage is terminal, the reaction temperature is about −70° to about 90° Centigrade, the reaction pressure is 0 to 1300 p.s.i.g. and the molar ratio of hydrogen sulfide to the allene compound is about 1.5:1 to about 15:1.

3. The process of claim 2 wherein the allene compound is a lower aliphatic allene and the mole ratio of hydrogen sulfide to the allene compound is about 2:1 to about 12:1.

4. The process of claim 3 wherein the allene compound is allene.

5. The process of claim 4 wherein the ultraviolet light of wavelength substantially above about 2600 Angstroms is provided by passing ultraviolet light through vitreous filter material which is transparent to at least some wavelengths of light in the 2600 to 3800 Angstroms wavelength region but is substantially opaque to light in the 100-2600 Angstroms wavelength region and the organic photosensitizing reagent is a carbonyl compound introduced in a concentration of about 0.001 to about 2 percent by weight of the reaction mixture.

6. The process of claim 5 wherein the photosensitizing reagent is an aryl carbonyl compound introduced in a concentration of about 0.01 to about 1 percent by weight of the reaction mixture.

7. The process of claim 6 wherein the photosensitizing reagent is a phenyl carbonyl compound charged in a concentration of about 0.1 to 0.5 percent by weight of the reaction mixture.

8. The process of claim 7 wherein the vitreous filter material is selected from the group consisting of Chemical Pyrex and Corex 9700.

9. The process of claim 8 wherein the vitreous filter material is Chemical Pyrex.

10. The process of claim 8 wherein the vitreous filter material is Corex 9700.

11. The process of claim 8 wherein the organic photosensitizing reagent is benzaldehyde.

12. The process of claim 8 wherein the photosensitizing reagent is acetophenone.

13. The substantially colorless sulfhydryl-terminated product of claim 1.

* * * * *